US00PP09107P

United States Patent [19]

Escande

[11] Patent Number: Plant 9,107

[45] Date of Patent: Apr. 18, 1995

[54] NECTARINE TREE—CRYSTAL ROSE

[76] Inventor: Jean L. Escande, 47500 Fumel, Saint Vite, France

[21] Appl. No.: 141,473

[22] Filed: Oct. 22, 1993

[51] Int. Cl.[6] ..... A01H 5/00

[52] U.S. Cl. ..... Plt./40.1

[58] Field of Search ..... Plt. 40.1

*Primary Examiner*—James R. Feyrer

*Attorney, Agent, or Firm*—Godfrey & Kahn

[57] ABSTRACT

A new and distinct variety of nectarine tree which is denominated varietally as "Crystal Rose" and which is ripe for commercial harvesting and shipment under the ecological conditions prevailing in San Joaquin Valley of Central California approximately June 21 through July 1, the tree of the subject variety producing fruit which have a red skin color, white flesh, is free stone and further has a firm flesh at commercial maturity.

1 Drawing Sheet

BACKGROUND OF THE NEW VARIETY

The present invention relates to a new and distinct variety of nectarine tree hereinafter denominated varietally as "Crystal Rose" and more particularly, to a nectarine tree which is somewhat remotely similar in its harvesting date to the nectarine tree Arctic Glo and Arctic Rose, (U.S. Plant Pat. Nos. 7,884 and 7,889 respectively) but which is distinguishable therefrom, and characterized principally as to novelty by producing fruit which have a larger size, noteworthy flavor, firm flesh and distinct flavor.

ORIGIN AND ASEXUAL REPRODUCTION OF THE NEW VARIETY

The inventor has spent a substantial portion of his professional life engaged in farming operations. In this regard, the applicant, in 1986, cross-pollinated a nectarine tree identified by the alpha-numeric designator NB 570 from his stock of nectarine trees, with that of a nectarine tree which has been denominated varietally as "Favols." The tree NB 570 is a non-released proprietary tree which applicant has retained for breeding purposes. The tree NB 570 produces a white fleshed, freestone nectarine. Further "Favols" produces a yellow fleshed, freestone nectarine. This cross pollination occurred at the inventor's farm which is located near Saint-Vite, France. The seeds from the cross-pollination were thereafter germinated and the new variety was grafted into commercial root stock which was then growing within the cultivated acreage of this same farm. The fruit produced by trees from the cross-pollination was evaluated in 1989 and were noted at that time to have desirable characteristics. The inventor subsequently marked one grafted tree for future observation. To determine whether the traits of the newly discovered variety were true, the inventor in 1989 removed bud wood from the original grafted tree and then grafted it into other test trees which were located on this same property. The inventor has continuously observed these test trees and the original grafted tree and has evaluated the fruit produced therefrom. It has subsequently been determined that the clonal progeny have the same identical characteristics as that observed in the selection resulting from the original cross pollination.

SUMMARY OF THE NEW VARIETY

The Crystal Rose nectarine tree hereof is characterized principally as to novelty by bearing fruit which are ripe for harvesting and shipment approximately seven days before the Arctic Rose nectarine tree [U.S. Plant Pat. No. 7,889] and approximately ten days after the Arctic Glo tree nectarine [U.S. Plant Pat. No. 7,884] in the San Joaquin Valley of Central California. In this regard, the variety is ripe for harvesting and shipment approximately June 21–July 1, and further is distinguishable from the above noted varieties by its large size, exceptional flesh firmness, and sweet flavor.

BRIEF DESCRIPTION OF THE DRAWING

The accompanying drawing is a color photograph of five mature fruit, one of which has been divided in the axial plane to show the flesh and pit characteristics, together with a twig bearing typical leaves which display the coloration of the top and bottom surfaces thereof, and a representative stone all of the subject variety.

DETAILED DESCRIPTION

Referring more specifically to the pomological details of this new and distinct variety of nectarine tree, the following has been observed under the ecological condition prevailing at the applicant's licensee's orchard which is located near Visalia, Calif. All major color code designations are by reference to the dictionary of color by Maerz & Paul, First Edition 1930, and alternatively by reference to the Inter-Society Color Council — National Bureau of Standards Color Charts. Common color names are also employed occasionally.

TREE

Size:

*Generally.*—Medium to large. Test trees of the new variety, which are (4) four years old range in size from about 90 to 96 inches in width when measured at the crown; and 12.0 to approximately 12.5 feet in height. These same trees were pruned to an average height during the winter of 1993–1994 to about 7.5 to about 8.5 ft. Since the pruning, the trees have developed 3 to 4 ft. of new growth.

Form:

*Generally.*—Upright to upright spreading. The final form of the tree is determined by pruning practices. The test trees are trained to an openvase system. These same trees have typically developed four main scaffolds.

Productivity: Productive.

Regularity of bearing: Regular.

Vigor: Vigorous, and hardy under the environmental conditions existing in the San Joaquin Valley of Central California.

BRANCHES

Size: Average, sturdy.

Surface texture: Average, smooth

Bark color: Grey-Brown, the color is not considered distinctive of the variety [8-J-10].

New growth:

*Color.*—Light green [17-k-7] (119.1 YG). A pale rose color appears where shoots are exposed to direct sunlight [4-I-9]. The color of new expanding shoots are bright green [18-L-5].

Mature growth:

*Color.*—Light grey-green [7-E-12].

Internode:

*Length.*—Generally considered to be average, that is, approximately 25 mm to 33 mm on current season hanger wood.

TRUNK

Size: Large, and sturdy. The test trees which are (4) four years old have developed trunks in the range of approximately 8.9 cm to 10.7 cm in diameter.

Surface texture: Relatively smooth.

Bark color: Dark, grey-brown [7-A-10 to approximately 7-C-8].

Lenticels:

*Generally.*—Numerous oval lenticels are present. These range in size from approximately 2 mm to 5 mm in width; and from 1 mm to approximately 2 mm in height.

LEAVES

Size:

*Generally.*—Large and narrow.

*Average length.*—Approximately 18.0 cm to about 22.6 cm including the petiole.

*Average width.*—Approximately 4.4 cm to 5.1 cm.

Surface texture: Normal for the species, glabrous.

Leaf form: Lanceolate to nearly linear lanceolate, with the leaf tip generally being in the same plane as the main body of the leaf. Leaf apices are considered acuminate, although occasionally the leaf apices appear slightly twisted sideways and reflexed downwards.

Leave blade angle: At the top of the leaf, this angle is quite small, however, the angle at the base is considered acute.

Marginal edge: Considered crenate. In this regard the crenations are viewed as being low, large, and at times irregular.

Color:

*Upper leaf surface.*—Dark green [23-L-9]. [126.d 01G].

*Lower leaf surface.*—Grey-green [22-K-7] [125.m 01G]

Mid vein:

*Size.*—Average.

Color.—A light green [19-F-5] [120.m YG].

LEAF PETIOLE

Length: Considered average in size, but long for the species. Average size is about 9 mm to about 13 mm in length and approximately 1.5 mm to 3 mm in thickness.

Petiole:

*Shape.*—Grooved.

*Color.*—A light green [19-J-8]. The color is somewhat darker within the petiole groove.

Leaf glands: Variable, and considered large in size. The leaf glands are most correctly characterized as reniform. In this regard, normally 2 to 5 glands are present on the petiole or just below the leaf margin. An additional 1 to 2 l reniform glands are normally present along the basal margin of the leaf blade itself. Occasionally, a stalked gland or glands may be formed on the petiole. The leaf glands are generally in alternate positions, and have a light yellow color which darkens with senescence.

*Color.*—A shiny, bright green [18-K-6].

Stipules:

*Generally.*—Stipules which are present may vary in length from 5 mm to 7 mm. Further, the stipules appear only at the base of the leaves and on the tips of new shoots. The stipules are considered early deciduous.

*Form.*—The stipule form is considered linearly lanceolate and further has a serrate margin.

*Color.*—The stipule color is considered a light green — yellow [17-L-6].

FLOWERS

Date of bloom: February 25 through March 5 under the ecological conditions prevailing in the San Joaquin Valley of Central California. The date of bloom is considered average for the species.

Flower size:

*Generally.*—Average; and having a showy type flower.

Fertility: Self fruitful.

Duration of flowering: Considered long.

Petal:

*Shape.*—Rounded.

*Number.*—Five.

*Size.*—Average for the species. The petal size is non-distinguishing.

Distribution of flower buds: The flower buds generally appear in groups of two or more.

Petal color at full flowering: The flower petals have a light pink color with a deeper pink color in the throat. Further, the apex of the petals are distinctly ruffled. Petal margin [C-1, Plate 50]; petal base [G-12, Plate 51].

Pistil: One pistil is always present.

Stamen:

*Generally.*—The length of the stamen is shorter than the length of the individual petals.

Anthers:

*Generally.*—Pollen is normally present on the anthers.

Ovaries:

*Generally.*—Present, and having no pubescence.

Calyx:

*Color.*—The color of the calyx prior to the petals falling off is considered greenish-yellow and is not particularly distinctive of the variety.

Flower buds:

*Generally.*—Considered hardy and well developed. The present variety requires a dormant period of approximately 500 hours at temperatures below 45° F.

FRUIT

Maturity when described: Ripe for commercial harvesting and shipment approximately June 21 through July 1 under the environmental conditions existeing in the San Joaquin Valley of Central California.

Size:

*Uniformity.*—Uniform, and considered large for the species.

*Average cheek diameter.*—Approximately 65 mm to 77 mm.

*Average suture diameter.*—Approximately 63 mm to 73 mm.

*Average axial diameter.*—Approximately 73 mm to 81 mm.

Form:

*Uniformity.*—Uniform and considered globose, in its apical aspect. The fruit is slightly ovate in its lateral aspect. The fruit is most frequently asymmetrical.

Suture:

*Generally.*—The fruit has a prominent ventral suture. In this regard, the suture appears as a slight indentation which extends from the base to the apex. The suture is more depressed over the apical shoulder near the apex. As a general matter, the suture appears as a smooth line, although slight clefting over the basal shoulders and the stem cavity may be evident. No stitching is evident. The suture takes on the coloration of the surrounding skin color, although occasionally it may take on a red color with narrow red striping. The color of the striping is usually dark red [5-L-11 to 6-L-11]. A slight depression is evident along the ventral suture and in close proximity to the apex.

Ventral surface:

*Generally.*—Uniformly rounded and occasionally moderately uneven and protruding. The sides usually appear unequal but may appear only slightly so. Moderate lipping is present, and is usually stronger on one side.

Stem cavity:

*Generally.*—Considered medium to small, uniformly flared, rounded, and having a moderate depth.

*Width.*—Approximately 25 mm to 31 mm.

*Length.*—Approximately 27 mm to 34 mm.

*Depth.*—Approximately 12 mm to 14 mm.

*Shape.*—Oval, and at times a crease is present where the branch has become indented into the shoulder of the fruit. The indented area is usually a ground color of light cream [9-C-2] to cream-green [17-E-2].

Fruit stem:

*Size.*—Approximately 6.0 mm to 8.5 mm in length; and approximately 3.0 mm to 4.0 mm in thickness.

*Color.*—Light olive-green [20-J-2].

Base:

*Generally.*—Variable, normally broad and well rounded, although it may appear truncate. The fruit base is distinctly oblique to the fruit axis.

Apex:

*Generally.*—Mucronated and firm.

Pistil point: Present and most frequency oblique.

Surface texture: Glabrous.

Skin:

*Thickness.*—Slightly thicker than average.

*Flavor.*—Mildly acidic.

*Tendency to crack.*—Not observed

*Tenacious to flesh.*—Yes, at commercial maturity, however, the skin will normally readily peel away from the flesh with advancing maturity.

*Pubescence.*—Absent.

*Color.*—Variable. A dark red, [7-J-6] (13.deep red), to a cherry red [4-K-9]. Although some pale yellow speckling may be evident [5-I-4]. As a general matter, however, the intensity of the red color does not vary from sun exposed to internal fruiting areas of the skin. A ground color is present in smaller amounts and ranges from a cream color [9-C-2] to a very pale green [17-E-2].

Flesh color: Generally considered white [1-A-1]. Although some small amounts of pink may be found in the flesh adjacent to the skin [12-K-8] (6. Pink).

Pit cavity:

*Color.*—The pit cavity has a cream coloration [11-E-1], [86.1.Y].

Flesh fibers:

*Length.*—Medium to long and having a white color.

*Numbers.*—Few.

*Texture.*—Fine and tender.

Flesh flavor: Rich.

Aroma: Moderate, distinct, and pleasant.

Flesh firmness: Crisp and firm. The flesh softens and becomes more juicy with advancing maturity.

Overall eating quality: Well above average. The flesh texture is uniformly firm and considered creamy.

Amygdalin: Not detected.

Ripening: The fruit first ripens along the ventral suture.

STONE

Generally: Considered semi-freestone to freestone. No air space is present in the pit cavity. The stone breaks free from the cavity with advancing maturity.

Size: Average.

*Stone length.*—Approximately 38 to 45 millimeters.

Stone width.—Approximately 26 to 29 millimeters.

Stone breadth.—Approximately 20 to 24 millimeters.

Form:

*Generally.*—Variable and irregular, most frequently the stone is slightly obovate, although at times it may appear oval.

Hilum:

*Shape.*—Narrow and indented. It may further appear heavily eroded.

Apex:

*Shape.*—Acuminate and abruptly pointed.

Stone sides:

*Shape.*—Nonuniform.

Surface texture: Irregularly furrowed and deeply pitted.

Fibers: Short fibers cling to the stone basally and along the base of both the ventral and dorsal sutures.

Stone base: The base is considered to be truncate in shape and the base angel is variable, although most frequently it is oblique to the fruit axis.

Ridges:

*Shape.*—Moderately rounded and considered interrupted.

Ventral edge:

*Shape.*—Serrated and nonuniform. The ventral edge is wide [7 mm to 9 mm] at mid-suture. Wings are present on the ventral suture and at times forms a strong keel basally which may protrude a distance of 4 mm to 6 mm out from the body of the stone. The ventral wings are most prominent from mid-suture to the stone base.

Dorsal edge:

*Generally.*—Considered pronounced and ridged and having a nonuniform shape. The dorsal edge is somewhat prominent and moderately eroded over the apical shoulders.

Color: Dry — light tan [11-F-4] [70.1. OY]. The color is not considered distinctive.

Tendency to split: Moderate.

Surface texture of seed: A brown coat is present, the color is not distinctive, however.

Fertility: Considered self-fruitful.

Use: A fresh market nectarine for both local and long distance shipping.

Keeping quality: Noteworthy.

Shipping quality: Excellent.

Resistance to disease: No particular susceptibilities were noted.

Although the new variety of nectarine tree possesses the described characteristics as a result of the growing conditions prevailing in the San Joaquin Valley of Central California, it is to be understood that variations in the usual magnitude and characteristics incident to growing conditions, fertilization, pruning and pest control are to be expected.

Having thus described and illustrated our new variety of nectarine tree what is claimed as new and desired to be secured by plant Letters Patent is:

1. A new and distinct variety of nectarine tree substantially as illustrated and described and which produces fruit which are ripe for commercial harvesting and shipment approximately seven days before the nectarine tree Arctic Rose (U.S. Plant Pat. No. 7,889) and approximately ten days after the nectarine tree Arctic Glo (U.S. Plant Pat. No. 7,884) at the same geographical location, and which is further distinguished as to novelty by having a large size, noteworthy flavor, and a white, firm flesh texture at commercial maturity.

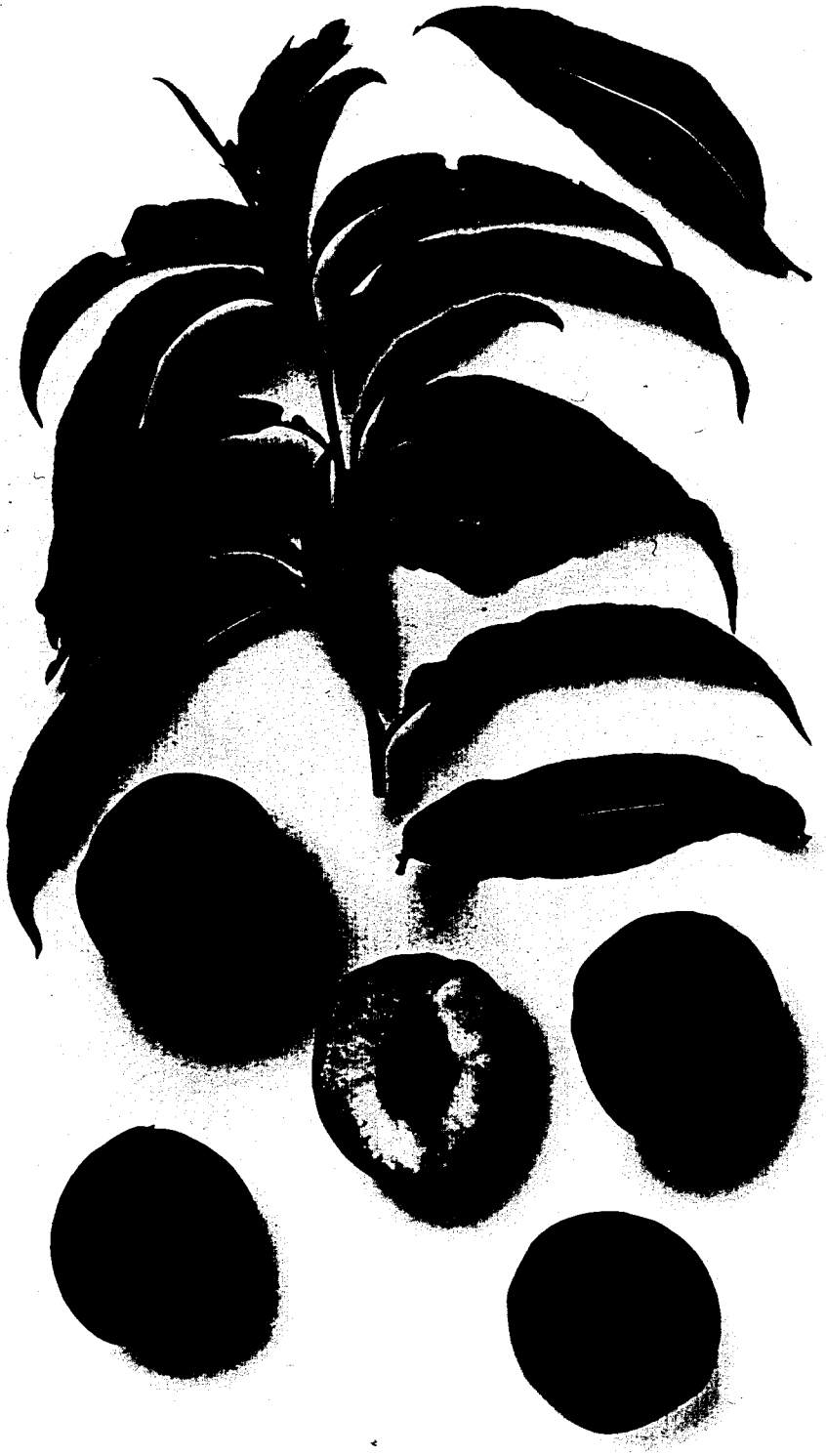

* * * * *